(12) United States Patent
Kwok (10) Patent No.: US 6,561,191 B1
(45) Date of Patent: *May 13, 2003

(54) MASK AND A VENT ASSEMBLY THEREFOR

(75) Inventor: Philip R. Kwok, Chatswood (AU)

(73) Assignee: ResMed Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/452,558

(22) Filed: Dec. 1, 1999

Related U.S. Application Data (63) Continuation-in-part of application No. 09/021,541, filed on Feb. 10, 1998.

(51) Int. Cl.[7] ................................................ A62B 18/10
(52) U.S. Cl. ........................... 128/207.12; 128/207.16; 128/205.25; 128/205.11; 128/205.24
(58) Field of Search .................... 128/207.12, 207.16, 128/207.13, 205.25, 205.11, 205.24, 203.11, 202.27, 204.18, 201.25

(56) References Cited

U.S. PATENT DOCUMENTS

| | | | |
|---|---|---|---|
| 781,516 A | 1/1905 | Guthrie | |
| 812,706 A | 2/1906 | Warbasse | |
| 835,075 A | * 11/1906 | Mahaffy | ................ 128/204.18 |
| 1,081,745 A | 12/1913 | Johnston et al. | |
| 1,192,186 A | 7/1916 | Greene | |
| 1,653,572 A | 12/1927 | Jackson | |
| 1,926,027 A | 9/1933 | Biggs | |
| 2,123,353 A | 7/1938 | Catt | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,872,923 A | * 2/1959 | Birch et al. | ............ 128/207.12 |
| 2,931,356 A | 4/1960 | Schwarz | |

(List continued on next page.)

FOREIGN PATENT DOCUMENTS

| | | |
|---|---|---|
| AU | 91/77110 B | 11/1991 |
| AU | 94/64816 B | 12/1994 |
| AU | 95/16178 B | 7/1995 |
| AU | A 32914/95 | 2/1996 |
| AU | 9459430 | 2/1996 |

(List continued on next page.)

OTHER PUBLICATIONS

Mask 1 Photographs, Respironics Inc., Reusable Full Mask (small) Part # 452033 Lot #951108.
Mask 2 Photographs, Puritan —Bennett, Adam Curcuit, Shell Part # 231700, Swivel Part # 616329–00, Pillows (medium) Part #616324.

(List continued on next page.)

*Primary Examiner*—Aaron J. Lewis
*Assistant Examiner*—Darwin Erezo
(74) *Attorney, Agent, or Firm*—Pillsbury Winthrop LLP (57) ABSTRACT

A mask (10) for use with a system for supplying breathable gas pressurised above atmospheric pressure to a human or animal's airways. The mask (10) includes a mask shell (12) which is, in use, in fluid communication with a gas supply conduit and a gas washout vent assembly (20). The gas washout vent assembly (20) includes at least one gas washout orifice (22) extending from a first side of the vent assembly (20) positioned, in use, adjacent the human or animal's face and a second side positioned, in use, adjacent the atmosphere. The cross-sectional area of the orifice (22) at the first side is larger than the cross-sectional area of the orifice (22) at the second side.

44 Claims, 4 Drawing Sheets

U.S. PATENT DOCUMENTS

| | | | |
|---|---|---|---|
| D188,084 S | 5/1960 | Garelick | |
| 2,939,458 A | 6/1960 | Lundquist | |
| 3,013,556 A | 12/1961 | Galleher | |
| 3,189,027 A | 6/1965 | Bartlett | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,796,216 A | 3/1974 | Schwarz | |
| 3,799,164 A | 3/1974 | Rollins | |
| D231,803 S | 6/1974 | Huddy | |
| 4,077,404 A | 3/1978 | Elam | |
| D250,131 S | 10/1978 | Lewis et al. | |
| 4,167,185 A | 9/1979 | Lewis | |
| 4,219,020 A | 8/1980 | Czajka | |
| 4,226,234 A | 10/1980 | Gunderson | |
| 4,245,632 A | 1/1981 | Houston | |
| 4,276,877 A * | 7/1981 | Ddulla | 128/200.27 |
| D262,322 S | 12/1981 | Mizerak | |
| 4,304,229 A | 12/1981 | Curtin | |
| 4,328,797 A | 5/1982 | Rollins, III et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,454,881 A | 6/1984 | Huber et al. | |
| 4,467,799 A | 8/1984 | Steinberg | |
| 4,522,639 A | 6/1985 | Ansite et al. | |
| 4,558,710 A | 12/1985 | Eichler | |
| 4,559,939 A * | 12/1985 | Levine et al. | 128/201.28 |
| 4,616,647 A | 10/1986 | McCreadle | |
| 4,622,964 A | 11/1986 | Flynn | |
| 4,648,394 A * | 3/1987 | Wise | 128/201.24 |
| 4,649,912 A * | 3/1987 | Collins | 128/202.13 |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Bellm | |
| 4,971,051 A | 11/1990 | Toffolon | |
| 4,974,586 A | 12/1990 | Wandel et al. | |
| 4,986,269 A | 1/1991 | Hakkinen | |
| 4,989,596 A * | 2/1991 | Macris et al. | 128/201.28 |
| 4,989,599 A | 2/1991 | Carter | |
| 5,005,568 A | 4/1991 | Loescher et al. | |
| 5,005,571 A | 4/1991 | Dietz | |
| 5,018,519 A | 5/1991 | Brown | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,046,512 A * | 9/1991 | Murchie | 128/848 |
| 5,063,922 A | 11/1991 | Hakkinen | |
| 5,065,756 A * | 11/1991 | Rapoport | 128/204.18 |
| 5,069,205 A | 12/1991 | Urso | |
| D323,908 S | 2/1992 | Hollister et al. | |
| 5,109,839 A * | 5/1992 | Blasdell et al. | 128/203.12 |
| 5,109,840 A | 5/1992 | Daleiden | |
| 5,121,745 A | 6/1992 | Israel | |
| 5,133,347 A | 7/1992 | Huennebeck | |
| 5,140,982 A | 8/1992 | Bauman | |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan et al. | |
| 5,265,595 A | 11/1993 | Rudolph | |
| 5,279,289 A | 1/1994 | Kirk | |
| 5,280,784 A | 1/1994 | Kohler | |
| 5,311,862 A * | 5/1994 | Blasdell et al. | 128/205.25 |
| 5,322,057 A | 6/1994 | Raabe et al. | |
| 5,343,878 A | 9/1994 | Scarberry et al. | |
| 5,357,951 A | 10/1994 | Ratner | |
| 5,372,130 A * | 12/1994 | Stern et al. | 128/205.25 |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A * | 7/1995 | Le Mitourad | 128/206.24 |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |
| RE35,339 E | 10/1996 | Rapoport | |
| 5,560,354 A | 10/1996 | Rapoport | |
| 5,570,682 A | 11/1996 | Johnson | |
| 5,570,689 A | 11/1996 | Starr et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,645,049 A | 7/1997 | Foley et al. | |
| 5,647,355 A | 7/1997 | Starr et al. | |
| 5,647,357 A | 7/1997 | Barnett et al. | |
| 5,649,532 A | 7/1997 | Oren | |
| 5,649,533 A | 7/1997 | Griffiths | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,732,695 A | 3/1998 | Metzger | |

| | | | |
|---|---|---|---|
| 5,746,201 A | 5/1998 | Kidd | |
| 5,813,423 A | 9/1998 | Kirchgeorg | |
| 5,832,918 A | 11/1998 | Pantino | |
| 5,921,239 A * | 7/1999 | McCall et al. | 128/205.25 |
| 6,006,748 A | 12/1999 | Hollis | |
| 6,019,101 A * | 2/2000 | Cotner et al. | 128/207.13 |

FOREIGN PATENT DOCUMENTS

| | | |
|---|---|---|
| AU | A 41018/97 | 4/1998 |
| AU | A 89312/98 | 1/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0 608 684 A1 | 8/1994 |
| EP | 0697 225 A2 | 7/1995 |
| EP | 0 697 225 | 7/1995 |
| EP | 178 925 A2 | 4/1996 |
| EP | 0 747 078 A2 | 12/1996 |
| EP | 0 821 978 | 2/1998 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 395 391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2236681 A * | 4/1991 ............ 128/205.25 |
| GB | 2 267 648 A | 12/1993 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WP 87/01950 | 4/1987 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Mask 3, Photographs, DeVilbiss Healthcare Inc., DeVilbiss Seal–Ring and CPAP Mask Kit (medium), Part 73510–669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510–668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.

* cited by examiner

MASK AND A VENT ASSEMBLY THEREFOR

This application is a continuation-in-part of Ser. No. 09/021,541 filed Feb. 10, 1998.

FIELD OF THE INVENTION

The present invention relates to a mask and a vent assembly therefor.

The mask and vent assembly according to the invention have been developed primarily for the venting of washout gas in the application of continuous positive airway pressure (CPAP) treatment in conjunction with a system for supplying breathable gas pressurised above atmospheric pressure to a human or animal. Such a system is used, for example, in the treatment of obstructive sleep apnea (OSA) and similar sleep disordered breathing conditions. However, the invention is also suitable for other purposes including, for example, the application of assisted ventilation or respiration.

The term "mask" is herein intended to include face masks, nose masks, mouth masks, nasal pillows, appendages in the vicinity of any of these devices and the like.

BACKGROUND OF THE INTENTION

Treatment of OSA by CPAP flow generator systems involves the continuous delivery of air (or other breathable gas) pressurised above atmospheric pressure to a patient's airways via a conduit and a mask.

For either the treatment of OSA or the application of assisted ventilation, the pressure of the gas delivered to a patient can be at a constant level, bi-level (ie. in synchronism with patient inspiration and expiration) or automatically adjusting in level to match therapeutic need. Throughout this specification the reference to CPAP is intended to incorporate a reference to any one of, or combinations of, these forms of pressure delivery.

The masks used in CPAP treatment generally include a vent for washout of the gas to atmosphere. The vent is normally located in the mask or in the gas delivery conduit adjacent the mask. The washout of gas through the vent is essential for removal of exhaled gases from the breathing circuit to prevent carbon dioxide "re-breathing" or build-up, both of which represent a health risk to the mask wearer. Adequate gas washout is achieved by selecting a vent size and configuration that will allow a minimum safe gas flow at the lowest operating CPAP pressure, which, typically can be as low as around 4 cm $H_2O$ for adults and 2 cm $H_2O$ in paediatric applications.

Prior art masks are generally comprised of a rigid plastic shell which covers the wearer's nose and/or mouth. A flexible or resilient rim (or cushion) is attached to the periphery of the shell which abuts and seals against the wearer's face to provide a gas-tight seal around the nose and/or mouth.

A prior art washout vent utilized one or more holes or slits in the rigid shell or in a rigid portion of the delivery conduit to allow the washout gas to vent to atmosphere. In some masks, the holes or slits were formed during the moulding process. In others, they were drilled or cut as a separate step after the shell or conduit had been moulded.

The flow of gas out the holes or slits in the shell or conduit to atmosphere creates noise and turbulence at the hole or slit outlet as the delivered gas, and upon expiration, the patient-expired gas (including $CO_2$) exits. Bi-level and autosetting gas delivery regimes tend to generate more noise than a constant level gas delivery regime. This is thought to be due to the extra turbulence created by the gas accelerating and decelerating as it cycles between relatively low and relatively high pressures. The noise adversely affects patient and bed-partner comfort.

Another prior art vent included hollow rivets or plugs manufactured from stainless steel or other rigid materials attached to openings in the rigid shell. The outer edges of the rivets were rounded to help reduce noise. However, this approach was expensive, required an extra production step and did not prove effective in reducing noise.

Another approach to reduce noise involved the use of sintered filters at the gas outlet of the mask shell. However, the filters were prone to blocking, especially in the presence of moisture. Accordingly, sintered filters were impractical for use in CPAP treatment as they were easily blocked by the moisture from the patient's respiratory system or humidifiers or during the necessary regular cleaning of the mask and associated componentry.

Foam filters wrapped around the air outlets in the shell were also attempted. However they also suffered from the disadvantages of being prone to blocking, difficult to clean and requiring constant replacement.

Remote outlet tubes have been used to distance the noise source from the patient. However, these tubes are difficult to clean, are prone to entanglement by the patient and/or their bed partner and suffer the further disadvantage that a volume of exhausted gas is retained in the tube adjacent the mask.

It is an object of the present invention to substantially overcome or at least ameliorate the prior art disadvantages and, in particular, to reduce the noise generated by gas washout through a mask.

SUMMARY OF THE INVENTION

Accordingly, the invention, in a first aspect, discloses a mask for use with a system for supplying breathable gas pressurised above atmospheric pressure to a human or animal's airways, the mask includes a mask shell which is, in use, in fluid communication with a gas supply conduit; and a gas washout vent assembly, the gas washout vent assembly includes at least one gas washout orifice extending from a first side of the vent assembly positioned, in use, adjacent the human or animal's face and a second side positioned, in use, adjacent the atmosphere and the cross-sectional area of the orifice at the first side is larger than the cross-sectional area of the orifice at the second side.

In a second aspect, the invention discloses a vent assembly for the washout of gas from a mask or conduit used with a system for supplying breathable gas pressurized above atmospheric pressure to a human or animal, the vent assembly includes at least one gas washout orifice extending from a first side of the vent assembly placed, in use, adjacent the human or animal's face to a second side placed, in use, adjacent the atmosphere, the cross-sectional area of the orifice at the first side is larger than the cross-sectional area of the orifice at the second side.

Preferably, the orifice includes a first substantially cylindrical portion adjacent the first side, a second cylindrical portion adjacent the second side and a tapering portion between the first and second substantially cylindrical portions.

Preferably also, the second substantially cylindrical portion and the tapering portion are of approximately equal thickness in the axial direction of the orifice and are thicker than the first substantially cylindrical portion.

Desirably, the vent assembly includes a plurality of said orifices therethrough.

Desirably also, each of said orifices is separated from the other(s) of said orifices by at least the diameter of the orifice at the second side.

BRIEF DESCRIPTION OF THE DRAWINGS

Preferred embodiments of the invention will now be described, by way of examples only, with reference to the accompanying drawings in which.

DESCRIPTION OF THE PREFERRED EMBODIMENTS

Figure 1:
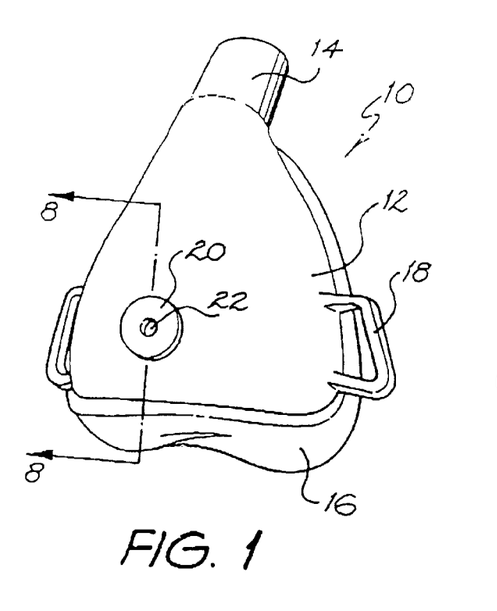
FIG. 1 is a perspective view of a first embodiment.
Figure 2:
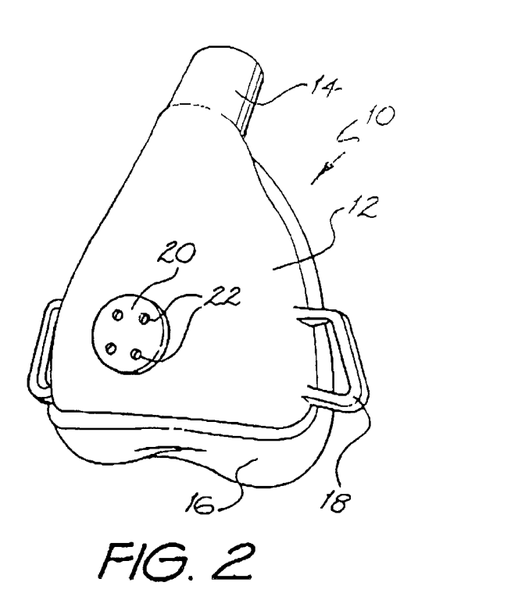
FIG. 2 is a perspective view of a second embodiment.

Referring firstly to FIG. 1, there is shown a mask 10 for use with a system (not shown) for supplying breathable gas pressurised above atmospheric pressure to a human or animal's airways. The mask includes a rigid plastics shell 12 having an inlet tube 14 for connection to a supply conduit to communicate breathable gas from a flow generator (not shown) to the nasal passages of the mask wearer. The mask shell 12 also includes a flexible sealing membrane 16 which is used to provide a gas tight seal between the face of the wearer and the interior of the shell 12. The shell 12 also includes lugs 18 for connecting the mask 10 to a head strap (not shown) to retain the mask in place.

Figure 8:
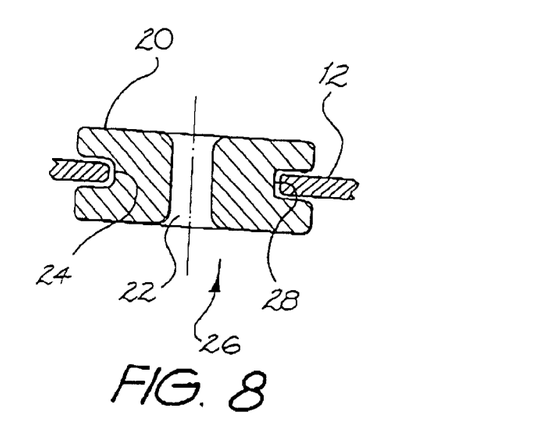
FIG. 8 is a partial cross-sectional view of the first embodiment along the line 8—8 of FIG. 1.

The mask includes a SILASTIC™ (a silicon-based polymer) insert 20 through which is provided an orifice 22 for gas washout. As best shown in FIG. 8, the insert 20 has a recess or groove 24 around its periphery. A correspondingly sized opening 26 bounded by a rim 28 is provided in the shell 12 to enable the insert 20 to be retained in place in the fashion of a grommet. The opening 26 can be moulded in the shell 12 or drilled or punched as a post moulding step. The flexibility of the SILASTIC™ allows the insert 20 to be initially squeezed through the opening 26 before resiliently expanding to the configuration shown in FIG. 8 and engaging the rim 28.

FIGS. 2 to 7 show further embodiments in which corresponding reference numerals are used to indicate like features. In all these embodiments the insert 20 has an external groove or recess 24 which engages the rim 28 of a corresponding shaped opening 26 in the mask shell 12 to retain the insert 20 in place.

In the embodiment shown in FIGS. 2 to 5 and 7 the insert 20 includes more than one orifice 22. In the embodiment shown in FIG. 6, two inserts 20 are provided in the shell 12.

Figure 9:
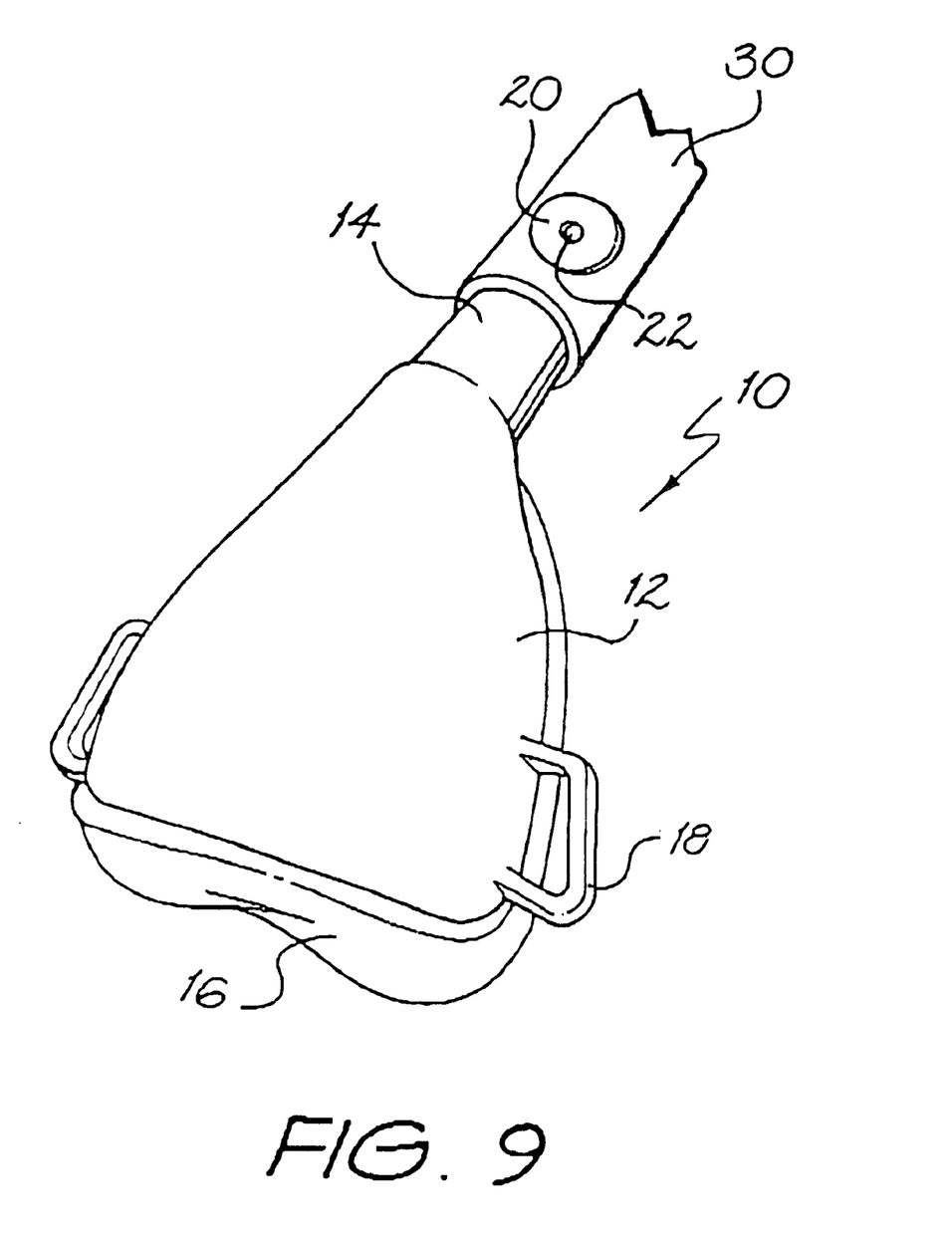
FIG. 9 is a perspective view of an eighth embodiment.

In the embodiment shown in FIG. 9, the insert 20 is provided in a gas supply conduit 30.

Figure 3:
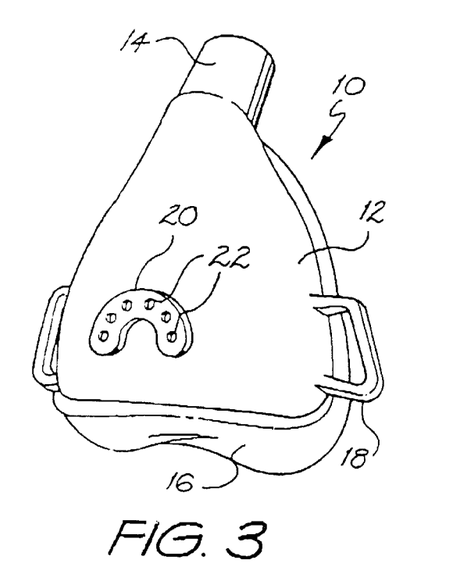
FIG. 3 is a perspective view of a third embodiment.
Figure 4:
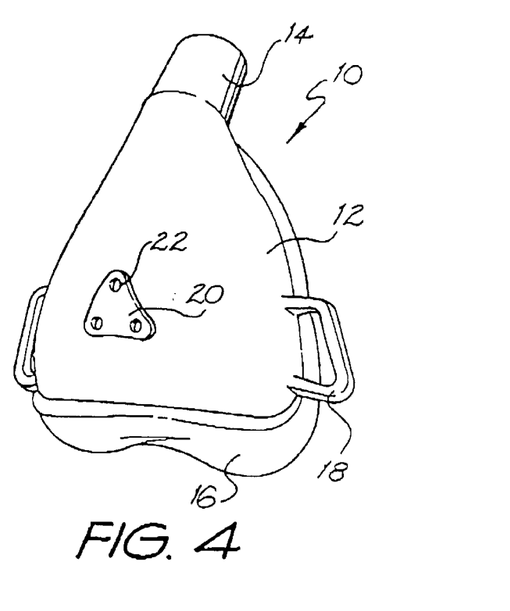
FIG. 4 is a perspective view of a fourth embodiment.
Figure 5:
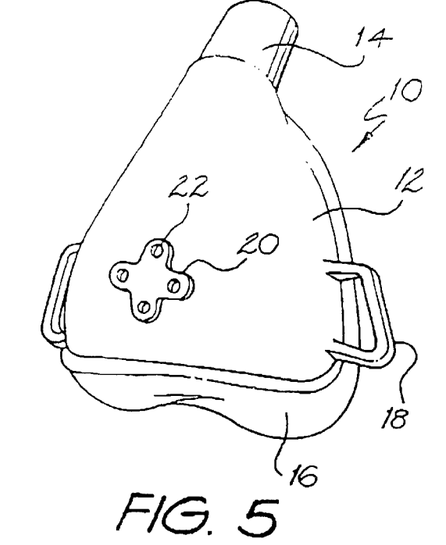
FIG. 5 is a perspective view of a fifth embodiment.
Figure 6:
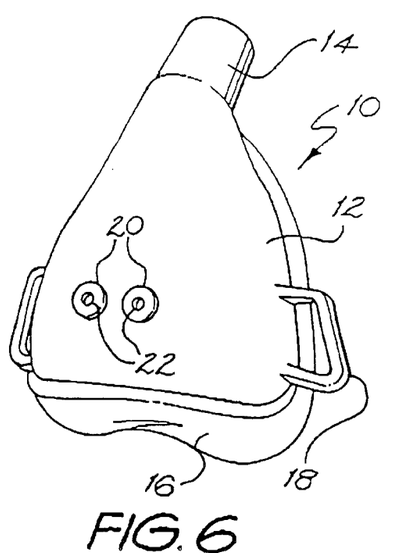
FIG. 6 is a perspective view of a sixth embodiment.
Figure 7:
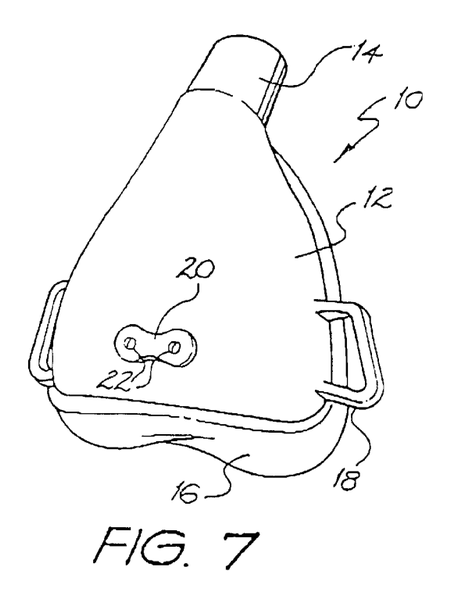
FIG. 7 is a perspective view of a seventh embodiment.
Figure 10:
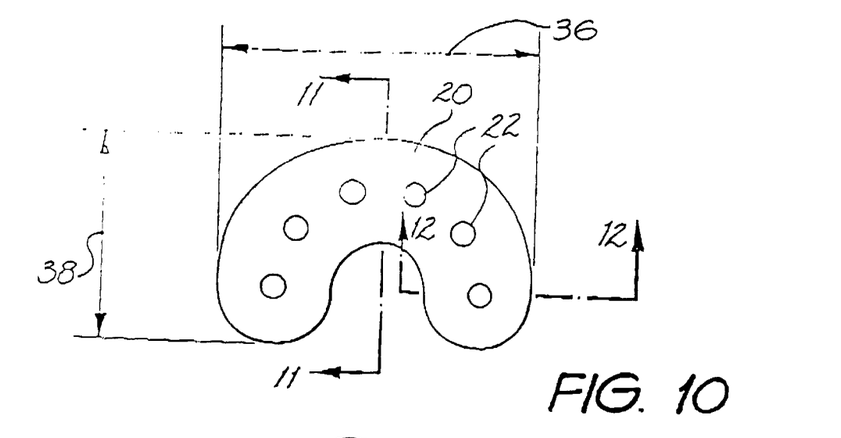
FIG. 10 is a plan view of the insert of the third embodiment.
Figure 11:
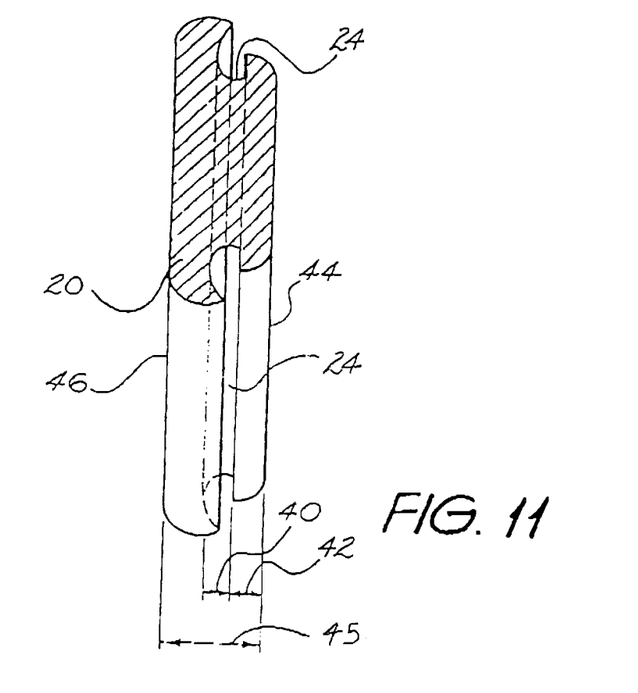
FIG. 11 is a cross-sectional view of the third embodiment insert along the line 11—11 of FIG. 10.
Figure 12:
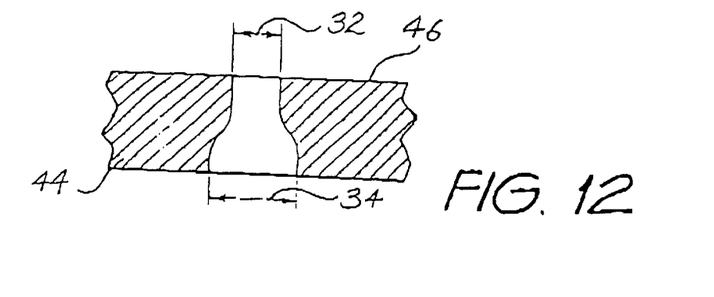
FIG. 12 is a partial cross-sectional view of the third embodiment insert along the line 12—12 of FIG. 10.

FIGS. 10 to 12 show the insert 20 of the third embodiment of FIG. 3. The dimensions 32, 34, 36, 38, 40, 42 and 45 are approximately diameter 1.73 mm, diameter 3.30 mm, 28.80 mm, 19.00 mm, 1.20 mm, 1.20 mm and 3.60 mm respectively.

The side 44 of the insert 20 faces the patient's face in use and the side 46 faces atmosphere.

The mask shell 12 is manufactured from polycarbonate. Other rigid plastics materials can equally be used. The insert 20 can be manufactured from an elastomer sold as SILASTIC™ (produced by the Dow Coming Corporation) or a thermoplastic elastomer sold as SANTOPRENE™ (produced by Monsanto). Other flexible elastomeric materials can be used also.

The mask 10 produces less noise than an identical mask having a similar sized and shaped orifice(s) formed directly in the mask shell 12 instead of formed in the flexible insert 20. It is thought that the noise reduction occurs due to the flexible insert 20 damping vibrations caused by air passage through the orifice(s) 22 which produce vibrations or similar in the mask shell 12.

A prototype of the embodiment of the invention shown in FIG. 3 has been tested over a range of constant and bi-level CPAP treatment pressures. For comparison purposes, an identical mask to that shown in FIG. 3 but formed entirely from polycarbonate and having six identical arcuately spaced holes 22 drilled directly through the mask shell was also tested. In both masks the six holes had a diameter of 1.7 mm The results of the test are summarised in the Tables below:

TABLE 1

Constant level gas delivery

| Pressure | Noise levels 1 m from mask (dBA) | |
| --- | --- | --- |
| (cm $H_2O$) | With flexible insert | Without flexible insert |
| 4 | 26.8 | 35.2 |
| 10 | 33.4 | 43.1 |
| 18 | 39.3 | 49.2 |

TABLE 2

Bi-level gas delivery

| Pressure | Noise levels 1 m from mask (dBA) | |
| --- | --- | --- |
| (cm $H_2O$) | With flexible insert | Without flexible insert |
| 5–10 | 30.8–38.5 | 37.2–43.0 |
| 10–15 | 38.6–43.7 | 42.9–47.9 |

As the results show, the mask shown in FIG. 3 produced less radiated noise than a similar mask not including the flexible elastomeric insert 20 representing a significant advantage in terms of the comfort of the mask wearer and their bed partner.

In addition to the noise reduction discussed above, the masks 10 possesses other advantages over those of the prior art. Firstly, the insert 20 is very easy to install into the mask shell 12 during either assembly of the mask which, is often supplied in kit form, or before and after cleaning which is regularly required and often carried out in the home environment. Secondly, the mask shell 12 may be produced with a single size of opening 26 and provided with a range of different inserts 20 which allows the outlet size to be "tuned"

to give an optimum gas washout rate for a particular patient's treatment pressure level.

Although the invention has been described with reference to specific examples, it will be appreciated by those skilled in the art, that the invention may be embodied in many other forms.

I claim:

1. A mask assembly for use with a system for supplying breathable gas pressurized above atmospheric pressure to a human or animal's airways, the mask assembly comprising:
   a mask that is, in use, in fluid communication with a gas supply conduit; and
   a gas washout vent assembly,
   wherein the gas washout vent assembly includes at least one gas washout orifice extending from an inner side of the vent assembly positioned, in use, adjacent the human or animal's face to an outer side positioned, in use, adjacent the atmosphere;
   wherein the gas washout orifice is open in use and a cross-sectional area of the orifice at the inner side vent assembly is larger than a cross-sectional area of the orifice at the outer side of the vent assembly; and
   wherein the inner side of the vent assembly extends inside the mask or conduit and the outer side of the vent assembly extends outside the mask or conduit.

2. A mask assembly as claimed in claim 1, wherein the orifice includes a first substantially cylindrical portion adjacent the inner side of the vent assembly, a second substantially cylindrical portion adjacent the outer side of the vent assembly and a tapering portion between the first substantially cylindrical portion and the second substantially cylindrical portion.

3. A mask assembly as claimed in claim 2, wherein the second substantially cylindrical portion and the tapering portion are of approximately equal thickness in the axial direction of the orifice and are thicker than the first substantially cylindrical portion.

4. A mask assembly as claimed in claim 1, wherein the vent assembly includes a plurality of said orifices therethrough.

5. A mask assembly as claimed in claim 4, wherein said orifices are separated from each other by at least the diameter of the orifice at the second side.

6. A mask assembly as claimed in claim 1, wherein at least one of the mask and the conduit is formed from a relatively rigid material and the vent assembly is an insert of relatively flexible elastomeric material and is attachable to one of the mask and the conduit.

7. A mask assembly as claimed in claim 6, wherein at least one of the mask and the conduit is formed from polycarbonate and the insert is formed from one of SILASTIC™ and SANTOPRENET™.

8. A mask assembly as claimed in claim 6, wherein the insert includes a groove around a periphery thereof, the groove being adapted to locate the insert against a correspondingly sized rim of an opening formed in one of the mask and conduit.

9. A mask assembly as claimed in claim 6, wherein the insert is substantially crescent shaped.

10. A mask assembly as claimed in claim 1, wherein an axis defined within the orifice extends substantially linearly from the inner side of the vent assembly to the outer side of the vent assembly.

11. A mask assembly as claimed in claim 1, wherein the orifice does not change shape upon application of pressurized gas.

12. A mask assembly as claimed in claim 1, wherein first and second ends of the orifice are located proximate an opening of the mask or conduit at, respectively, the inner side of the vent assembly and the outer side of the vent assembly.

13. A mask assembly as claimed in claim 1, wherein a thickness of the vent assembly is greater than an inner diameter of the orifice.

14. A mask assembly as claimed in claim 13, wherein a ratio of the thickness of the vent assembly to an outer diameter of the orifice is about 2.

15. A mask assembly as claimed in claim 14, wherein a ratio of a length of the orifice to a thickness of the mask or conduit is about 3.

16. A mask assembly for use with a system for supplying breathable gas pressurized above atmospheric pressure to a human or animal's airways, the mask assembly comprising:
   a mask that is, in use, in fluid communication with a gas supply conduit; and
   a gas washout vent assembly including at least one gas washout orifice extending from an inner side of the vent assembly positioned, in use, adjacent the human or animal's face to an outer side positioned, in use, adjacent the atmosphere,
   wherein a cross-sectional area of the orifice at the inner side of the vent assembly is larger than a cross-sectional area of the orifice at the outer side of the vent assembly; and
   wherein the orifice includes a first substantially cylindrical portion adjacent the inner side, a second substantially cylindrical portion adjacent the outer side and a tapering portion between the first substantially cylindrical portion and the second substantially cylindrical portion.

17. A mask assembly as claimed in claim 16, wherein the second substantially cylindrical portion and the tapering portion are of approximately equal thickness in the axial direction of the orifice and are thicker than the first substantially cylindrical portion.

18. A mask assembly as claimed in claim 16, wherein the tapering portion is present independent of whether the mask is in use.

19. A mask assembly as claimed in claim 16, wherein a thickness of the vent assembly is greater than an inner diameter of the orifice.

20. A mask assembly as claimed in claim 19, wherein a ratio of the thickness of the vent assembly to an outer diameter of the orifice is about 2.

21. A mask assembly as claimed in claim 20, wherein a ratio of a length of the orifice to a thickness of the mask or conduit is about 3.

22. A mask for use with a system for supplying breathable gas pressurized above atmospheric pressure to a human or animal's airways, the mask assembly comprising:
   a mask that is, in use, in fluid communication with a gas supply conduit; and
   a gas washout vent assembly, the gas washout vent assembly including at least one gas washout orifice extending from an inner side of the vent assembly positioned, in use, adjacent the human or animal's face to an outer side positioned, in use, adjacent the atmosphere,
   wherein a cross-sectional area of the orifice at the inner side of the vent assembly is larger than a cross-sectional area of the orifice at the outer side of the vent assembly;
   wherein the vent assembly includes a plurality of said orifices therethrough and said orifices are separated from each other by at least the diameter of the orifice at the outer side of the vent assembly, and wherein the inner side of the vent assembly extends inside the mask or conduit and the outer side of the vent assembly extends outside the mask or conduit.

23. A vent assembly for washout of gas from a mask or conduit used with a system for supplying breathable gas pressurized above atmospheric pressure to a human or animal, the vent assembly including at least one gas washout orifice extending from an inner side of the vent assembly placed, in use, adjacent the human or animal's face to an outer side placed, in use, adjacent the atmosphere, the gas washout orifice being open in use, and a cross-sectional area of the orifice at the inner side of the vent assembly is larger than a cross-sectional area of the orifice at the outer side of the vent assembly; wherein the orifice includes a first substantially cylindrical portion adjacent the inner side of the vent assembly, a second substantially cylindrical portion adjacent the outer side of the vent assembly and a tapering portion between the first substantially cylindrical portion and the second substantially cylindrical portion; wherein the second substantially cylindrical portion and the tapering portion are of approximately equal thickness in the axial direction of the orifice and are thicker than the first substantially cylindrical portion.

24. A vent assembly for washout of gas from a mask or conduit used with a system for supplying breathable gas pressurized above atmospheric pressure to a human or animal, the vent assembly including at least one gas washout orifice extending from an inner side of the vent assembly placed, in use, adjacent the human or animal's face to an outer side placed, in use, adjacent the atmosphere, wherein a cross-sectional area of the orifice at the inner side of the vent assembly is larger than a cross-sectional area of the orifice at the outer side of the vent assembly; wherein the vent assembly includes a plurality of said orifices therethrough and said orifices are separated from each other by at least the diameter of the orifice at the outer side and wherein the inner side of the vent assembly extends inside the mask or conduit and the outer side of the vent assembly extends outside the mask or conduit.

25. A vent assembly as claimed in claim 24, wherein an axis defined within the orifice extends substantially linearly from the inner side of the vent assembly to the outer side of the vent assembly.

26. A vent assembly as claimed in claim 24, wherein the orifice does not change shape upon application of pressurized gas.

27. A vent assembly as claimed in claim 24, wherein first and second ends of the orifice are located proximate an opening of the mask or conduit at, respectively, the inner side of the vent assembly and the outer side of the vent assembly.

28. A mask assembly for use with a system for supplying breathable gas pressurized above atmospheric pressure to a human or animal's airways, the mask assembly comprising:
  a mask that is, in use, in fluid communication with a gas supply conduit; and
  a gas washout vent assembly located on one of the mask and the conduit,
  wherein the gas washout vent assembly comprises an elastic, deformable insert that can be removably inserted into an opening provided on one of the conduit and the mask, the insert including a first surface to engage an inner surface of the mask or conduit, a second surface to engage an outer surface of the mask or conduit and a groove between the first and second surfaces to receive an edge defining the opening of the mask shell or conduit;
  wherein the insert includes at least one gas washout orifice, the orifice extending from an inner side of the insert positioned, in use, adjacent the human or animal's face to an outer side of the insert positioned, in use, adjacent the atmosphere,
  wherein an axis defined within the orifice extends substantially linearly from the inner side of the insert to the outer side of the insert, and
  wherein the orifice does not substantially change shape upon application of pressurized gas.

29. A mask assembly as claimed in claim 28, wherein the inner side of the insert extends inside the mask or conduit and the outer side of the insert extends outside the mask or conduit.

30. A mask assembly as claimed in claim 28, wherein a cross-sectional area of the orifice at the inner side of the insert is larger than a cross-sectional area of the orifice at the outer side of the insert.

31. A mask assembly as claimed in claim 30, wherein the orifice includes a first substantially cylindrical portion adjacent the inner side of the insert, a second substantially cylindrical portion adjacent the outer side of the insert and a tapering portion between the first substantially cylindrical portion and the second substantially cylindrical portion.

32. A mask assembly as claimed in claim 28, wherein an inner side of the orifice extends into the mask or conduit and an outer side of the orifice extends outside the mask or conduit.

33. A mask assembly as claimed in claim 28, wherein first and second ends of the orifice are located proximate the opening of the plenum chamber or conduit at, respectively, the first surface of the insert and the second surface of the insert.

34. A mask assembly as claimed in claim 28, wherein a thickness of the insert is greater than an inner diameter of the orifice.

35. A mask assembly as claimed in claim 34, wherein a ratio of the thickness of the insert to an outer diameter of the orifice is about 2.

36. A mask assembly as claimed in claim 35, wherein a ratio of a length of the orifice to a thickness of the groove is about 3.

37. An assembly for use with a system for supplying breathable gas pressurized above atmospheric pressure to a patient's airways, the mask assembly comprising:
  a plenum chamber including an air inlet tube that is, in use, in fluid communication with a gas supply conduit,
  a patient interface coupled to the plenum chamber and adapted to interface with the patient, and
  a gas washout vent assembly including at least one gas washout orifice extending from an inner side of the plenum chamber positioned, in use, adjacent the patient's face to an outer side of the plenum chamber positioned, in use, adjacent the atmosphere, the orifice being open in use and having a cross-sectional area at the inner side that is larger than a cross-sectional area at the outer side, wherein
  the outer side of the orifice is substantially circular,
  the orifice includes a central portion connecting the inner and outer sides, the central portion having a cross-sectional area that varies along a length of the central portion,
  the plenum chamber is defined by a wall structure made of a relatively rigid material and the vent assembly is made of a relatively flexible material compared to the rigid material of the mask, the vent assembly comprises an insert that can be removably inserted into an opening on one of the plenum chamber and the conduit, the insert including a first surface to engage an inner surface of one of the plenum chamber and the conduit, a second surface to engage an outer surface of one of the plenum chamber and conduit, and a groove provided between the first and second surfaces to receive a rim of the opening;

an axis defined along the central portion extends substantially linearly from the first surface of the insert to the second surface of the insert;

the orifice does not change shape upon application of pressurized gas; and a first end of the orifice is located proximate the opening of the plenum chamber or conduit at the first surface of the insert and a second end of the orifice is located proximate the opening of plenum chamber or conduit at the second surface of the insert.

38. The assembly as claimed in claim 37, wherein the patient interface comprises one of a cushion and nasal pillows.

39. An assembly as claimed in claim 37, wherein a thickness of the insert is greater than an inner diameter of the orifice.

40. An assembly as claimed in claim 39, wherein a ratio of the thickness of the insert to an outer diameter of the orifice is about 2.

41. An assembly as claimed in claim 40, wherein a ratio of a length of the central portion of the orifice to a thickness of the groove is about 3.

42. A vent assembly for washout of gas from a mask or conduit used with a system for supplying breathable gas pressurized above atmospheric pressure to a human or animal, the vent assembly including at least one gas washout orifice extending from an inner side of the vent assembly placed, in use, adjacent the human or animal's face to an outer side placed, in use, adjacent the atmosphere, the gas washout orifice being open in use, and a cross-sectional area of the orifice at the inner side of the vent assembly is larger than a cross-sectional area of the orifice at the outer side of the vent assembly; wherein the orifice includes a first substantially cylindrical portion adjacent the inner side of the vent assembly, a second substantially cylindrical portion adjacent the outer side of the vent assembly and a tapering portion between the first substantially cylindrical portion and the second substantially cylindrical portion; wherein a thickness of the vent assembly is greater than an inner diameter of the orifice.

43. A vent assembly as claimed in claim 42, wherein a ratio of the thickness of the vent assembly to an outer diameter of the orifice is about 2.

44. A vent assembly as claimed in claim 43, wherein a ratio of a length of the orifice to a thickness of the mask or conduit is about 3.

\* \* \* \* \*

UNITED STATES PATENT AND TRADEMARK OFFICE
CERTIFICATE OF CORRECTION

PATENT NO. : 6,561,191 B1
DATED : May 13, 2003
INVENTOR(S) : Kwok

It is certified that error appears in the above-identified patent and that said Letters Patent is hereby corrected as shown below:

<u>Title page,</u>
Insert item:
-- [30]    Foreign Application Priority Data
February 10, 1997     (AU) ……………... PO5045 --

Signed and Sealed this

Second Day of March, 2004

JON W. DUDAS
*Acting Director of the United States Patent and Trademark Office*